United States Patent [19]

Baranczuk

[11] 4,433,056
[45] Feb. 21, 1984

[54] PROCESS FOR PREPARATION OF CONTROL FOR USE IN ESTROGEN RECEPTOR TEST

[76] Inventor: Richard J. Baranczuk, 10127 Horton, Overland Park, Kans. 66202

[21] Appl. No.: 332,609

[22] Filed: Dec. 21, 1981

Related U.S. Application Data

[63] Continuation-in-part of Ser. No. 305,108, Sep. 24, 1981.

[51] Int. Cl.$^3$ ............................ G01N 33/50; G01N 33/74
[52] U.S. Cl. .................................. 436/8; 436/63; 436/503; 436/174; 435/1
[58] Field of Search ............... 252/408; 436/503, 8, 436/63, 174–178; 435/1

[56] References Cited

U.S. PATENT DOCUMENTS

| | | | |
|---|---|---|---|
| 3,854,470 | 12/1974 | Augspurger | 128/1 R |
| 3,866,598 | 2/1975 | Augspurger | 435/1 |
| 3,901,654 | 8/1975 | Gross . | |
| 3,906,929 | 9/1975 | Augspurger | 435/1 |
| 4,215,102 | 7/1980 | Lee | 424/3 |
| 4,232,001 | 11/1980 | Jensen et al. | 424/1 |
| 4,254,095 | 3/1981 | Fisher . | |
| 4,293,536 | 10/1981 | Jensen et al. | 436/503 |

OTHER PUBLICATIONS

Bojar et al., Cancer, vol. 46, pp. 2770–2774, (1980).
Koenders et al., J. Steroid Biochemistry, vol. 9, pp. 947–950, (1978).
Holt et al., Endocrinology, vol. 108(6), pp. 2308–2315, (6-1981).

*Primary Examiner*—Brooks H. Hunt
*Assistant Examiner*—M. Morkowitz
*Attorney, Agent, or Firm*—Litman, Day & McMahon

[57] ABSTRACT

A process is disclosed for producing steroid hormone receptor samples to be utilized as controls during assays of various human tissue for steroid hormones, especially estrogen. The process comprises collecting tissue known to include such receptors, adding a buffer solution to the tissue, homogenizing the tissue and buffer solution, centrifuging the homogenized mixture, and thereafter collecting the supernatant. The supernatant which contains the desired receptors is subdivided into suitable control sample size and preferably lyophilized to a flake.

10 Claims, No Drawings

PROCESS FOR PREPARATION OF CONTROL FOR USE IN ESTROGEN RECEPTOR TEST

CROSS-REFERENCE TO RELATED APPLICATION

The present application is a continuation-in-part of applicant's co-pending application entitled PROCESS FOR PREPARATION OF CONTROL FOR USE IN ESTROGEN RECEPTOR TESTS, Ser. No. 305,108, filed Sept. 24, 1981, pending.

BACKGROUND OF THE INVENTION

The present invention relates to production of control samples for use during testing for steroid receptors in human tissue. It is current medical theory that various steroid hormones such as glucocorticoids and mineralocorticoids and even those hormones which are normally considered sex hormones such as androgens, estrogens and progestins are present in both male and female humans. It is further medical theory that proteins called receptors are present in target cells within specific organs which selectively attract or hold the various steroid hormones within the particular organ.

It is often medically important to determine whether particular receptors are present in certain tissue in a human. In particular, it has been found that various steroids may be advantageously utilized to treat carcinoma. In the past cancer has frequently been attacked by utilization of cytotoxic chemotherapy or radiation therapy under the premise that, although chemotherapy or radiation kills a certain number of noncancerous cells throughout the body, this treatment will kill a higher percentage of the cancerous cells and thereby, presumably, control or eradicate the cancer. In this process the damage to healthy tissue within the body can be extensive. Therefore, it is desirable to find a substance which will be selectively toxic to cancerous cells.

One particular way of treating cancerous cells in a specific manner, has been the development of what is called endocrine therapy wherein steroid hormones are utilized to attack cancerous growths in specific organs. A secondary advantage of such treatment is that even if the cancer metastasizes and begins to spread throughout the body, the cancerous cells will still have the particular receptors of the organ from which the cancer originated and, therefore, will be selectively attacked by the hormones. Unfortunately, it has been found that many cancerous tumors at some stage of their development modify the structure of the cells therein so as to preclude the receptors and/or their production.

If the receptors are not present in the cancerous cells, then endocrine therapy will at best be a waste of time and may actually do more damage than good. If the receptors are not present, it is important to determine this early so that other treatment such as chemotherapy or radiological treatment can be initiated as soon as possible. Thus, it has become important to assay a cancerous tumor in order to determine whether any of the desired receptors are present. It is further important to ensure that any test related to presence of receptors in such tissue include simultaneous testing of known control samples so as to ensure the accuracy of the assay. The various steroid hormones are in common supply in mammal tissue, especially in organs which are activated by a specific steroid hormone. Unfortunately, the receptor protein is extremely heat laible and is very easily destroyed or rendered inert by separation from its parent live tissue for even short periods of time at room temperature. Freezing the tissue containing the receptor to a temperature in a range of solid carbon dioxide or liquid nitrogen will maintain the vitality of the protein for a longer period of time but does not provide a suitable sample with which to work and requires cumbersome cryogenic packaging and short travel time to prevent warming and destruction of the sample. The process of the present invention provides for production of a sample which is in a form which is easy to use, vital for long periods of time, and can be stored at room temperature.

Of particular interest in the area of endocrine therapy is the treatment of breast cancer with progesterone or, special estrogen hormones by processes, as described above. It has been found in certain medical testing that patients with breast cancer having a high estrogen receptor value respond poorly to chemotherapy as compared to patients with low estrogen receptor values. For instance, on a whole, women before menopause respond to chemotherapy with a substantially lower success rate than women who are post menopausal. Also, patients with high estrogen receptor values respond very favorably to endocrine therapy, whereas those with low receptor values respond very poorly to endocrine treatment. It is therefore important for an attending physician to determine whether estrogen receptors are abundant within the breast tumor. It is noted that estrogen receptors may be present in breast cancers of both men and women.

OBJECTS OF THE INVENTION

Therefore, the objects of the present invention are: to provide a process for the production of a control ample for use in steroid hormone receptor assays; to provide such a process wherein the control sample is stable; to provide such a process wherein the control sample is produced by collecting tissue known to contain the desired receptors, adding a buffer solution to the tissue, homogenizing the buffer and tissue, and thereafter centrifuging the tissue and buffer so as to form a supernatant which is aliquoted into portions for use as control samples; to provide such a process wherein the concentration of receptors, especially estrogen receptors, is enhanced before collection of the tissue by superovulation processes; to provide such a process wherein the supernatant is lyophilized or freeze dried to form a dry flake which is stable at room temperature while being contained in a vacuum; to provide such a process wherein a control sample of estrogen receptors is produced for use in conjunction with estrogen receptor assays in breast cancer; to provide such a process resulting in control samples which have reproducible assay characteristics; to provide a control sample for steroid hormone receptor assays which is stable in nature and transportable at room temperature; and to provide such a control sample which is relatively inexpensive to produce, easy to manufacture and particularly adapted for the intended purpose thereof.

Other objects and advantages of this invention will become apparent from the following description wherein is set forth, by way of example, certain embodiments of this invention.

SUMMARY OF THE INVENTION

A process is provided for the production of a control sample for use in steroid hormone receptor assays comprising the steps of collecting a tissue from an animal containing the steroid hormone receptor, adding a matrix or buffer solution to the tissue, homogenizing the tissue with the buffer solution therein, thereafter centrifuging the tissue and buffer whereupon a resultant supernatant liquid is collected for use as a control sample. Preferably, the supernatant is frozen to approximately the temperature of solid carbon dioxide, that is −78.c degrees centigrade (C.).

Preferentially, the concentration of receptors within the collected animal tissue is artifically enhanced while the tissue is still in the animal.

Typical of the steroid hormones are the estrogens (including estradiol, estrone, and estriol), progestins (including progesterone), androgens (including testosterone, androsterone, androstenedione and etiocholanolone), mineralocorticiods (including aldosterone) and glucocorticoids (including cortisol, corticosterone, cortisone, and corticosteroid).

The estrogen receptor sites may be found in such organs as the hypothalamus, pituitary, breasts, ovaries, fallopian tubes, cervix, vagina, uterus, placenta, adrenal cortex, and even in the testes. The progestins may be found in such organs as the ovaries, fallopian tubes, uterus, breasts, placenta, and the corpus luteum during an associated portion of the menstrual cycle. The androgens are frequently found in the testes, adrenal cortex, ovaries and hypothalamus. The mineralocorticoids are often found in the kidneys and adrenal cortex. The glucocorticoids are normally found in the liver, hypothalamus, and adrenal cortex.

The concentration of estrogen receptors in animal tissue, such as rabbit uterus, is enhanced by inducing superovulation within the animal in conjunction with mating prior to removal of the tissue for further processing.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific process and functional details disclosed herein are not to be interpreted as limiting, but merely as a basis for the claims and as a representative basis for teaching one skilled in the art to variously employ the present invention in virtually any appropriately detailed process.

A control sample is provided to use in an assay for the detection of estrogen receptors within cancerous breast cells so as to allow a basis for decisions regarding the optimum treatment to be utilized. The control sample comprises estrogen receptors in a stable state at room temperature. The control sample receptors are removed from animal, including human, tissue containing same and treated to maintain vitality at room temperature.

To initiate preparation of a steroid receptor control sample, it is preferable to select a tissue which will have a maximum concentration of the desired steroid hormone receptors and is sufficiently abundant and inexpensive to provide a satisfactory quantity of tissue to work with. For estrogen receptors, it has been found that the uterus, either whole or portions thereof, of a six day pregnant rabbit is relatively high in such receptors and makes a good source for tissue to produce the estrogen receptor sample. In addition, rabbits ovulate upon mating and it is, therefore, relatively easy under controlled conditions, to determine when the sixth day of pregnancy occurs. Preferably, the tissue having a high quantity of receptors is segregated and collected. The tissue is also preferably frozen immediately upon removal from the rabbit so as to prevent degradation of the receptor protein. Preferably, the tissue is frozen in an environment of solid carbon dioxide (that is, dry ice at −78.5 degrees C.) or liquid nitrogen. When sufficient tissue is collected to prepare the samples, the tissue is finely shreaded which may consist of slivering with a sharp knife or even pulverization.

It has been found that the concentration of estrogen receptors within the uterus of a six day pregnant rabbit can be enhanced if the rabbit is induced to superovulate in conjunction with mating. Methods of inducing superovulation are known. In particular, one method of inducing superovulation in a rabbit is to inject 0.15 milligram of follicle stimulating hormone (FSH) into the rabbit twice a day for two days, followed by two injections of 1.0 milligram of FSH on a third day, thereafter followed by injection of 25 international units of human chorionic gonadotropin (HCG) on the morning of mating. Alternatively, superovulation may be induced by substitution of pregnant mare's serum (PMS) for FSH and luteinizing hormone (LH) for HCG, although the injection amounts are varied due to slightly different half life of the various compositions in the body of the animal. It is further noted that the amounts of compositions utilized to induce superovulation are varied with the animal, thus, mammals other than rabbits would require different amounts which are generally known by those in the art to induce superovulation in such animals.

After shreading the tissue, a buffer solution is added thereto. The buffer eventually acts as a matrix into which the receptor protein is taken. Control of pH is preferably maintained at approximately 7.4. Although the receptor proteins can withstand some variation in pH, a substantial amount of variation will result in destruction of the protein. A suitable buffer comprises 504 grams per liter of 1.5 millimole ethylenediaminethetraacetic acid (EDTA) (preferably disodium) and 1.58 grams per liter of 10 millimole Tris-HCl [Tris hydroxy methyl aminomethane hydrochloride] which will hereinafter be referred to as Tris buffer. Also preferably, the Tris buffer is utilized in a ratio of approximately 1,000 parts by volume to one part of monothioglycerol and/or dithiothreitol which function to buffer sulfhydryl groups.

The tissue and the buffer are thereafter homogenized in a manner such that the integrity and architecture of the cells of the tissue are broken so as to release the receptors. At least a portion of the receptors are soluble within the buffer solution. In order to homogenize the tissue and buffer, it has been found that a small blender having a capacity of approximately five millimeters is suitable. It is important to continue to protect the receptor protein from overheating during the homogenization process, as such process works, the tissue and buffer solutions substantially thereby imparting heat into the consequent mixture. In order to avoid overheating, it has been found that running the blender for short periods of approximately ten seconds and thereafter cooling the mixture in an ice bath for at least one minute before again running the blender, will prevent overheating. Typically about three bursts of ten seconds each duration are necessary to suitably homogenize the mixture.

After the homogenization, the mixture is placed in a centrifuge. Preferably, the centrifuge is of the ultra type and it has been found that a centrifuge running at approximately forty thousand revolutions per minute or two hundred kilo gs operating on the mixture for approximately one half hour provide satisfactory results. The centrifuged material is carefully separated so as to prevent intermixing of the various layers. Often there will be a heavy portion consisting of cellular debris above which is a supernatant liquid layer covered by a layer of oil or fat. The supernatant is withdrawn from the remainder of the centrifuge mixture and collected. This supernatant contains the desired receptor proteins. The supernatant liquid is preferably immediately refrozen to less than $-70$ degrees C. by submerging in liquid nitrogen or the like.

The supernatant either before or after freezing is separated into aliquots of preferably substantially equal volume of suitable size for use in eventual comparison or control sample testing. The frozen aliquots are lyophilized or freeze dried in a vacuum. During the freeze drying process the temperature of the aliquots may be maintained at $-70$ degrees C. or raised so that the temperature approaches room temperature near the completion of the drying process. The resulting composition is a dry flake which may have many forms including being plate like or powder like. The flakes are very hygroscopic and are preferably maintained in a moisture free state until such time as they are utilized as a control. A suitable method of maintaining the flakes in a moisture free state comprises sealing the flakes in a bottle or container while still under vacuum, so that the flakes are subjected to the vacuum until the sealed container is opened for final disposition of the flakes.

The flakes are ultimately utilized as a comparison or control sample in a steroid hormone receptor assay. In particular, the flakes provide a predeterminable quantity of a particular receptor protein for use in a receptor protein test or assay against which cancerous tissue excised from a patient can be compared to ensure the efficiency and validity of the test. Such a test may be quantitative or qualitative. Suitable tests for determining presence of receptor proteins are known in the art. For example, a test kit is distributed for determination of estrogen receptors in breast cancer tissue by New England Nuclear Corporation. It is noted that the concentration of estrogen receptors in tissue is very small and is often less than $10^{-15}$ parts by weight of the tissue structure.

The following examples are offered to illustrate various embodiments of the present invention and the invention is not intended to be limited thereto.

EXAMPLE 1

Female rabbits are induced to superovulate by injections of FSH and HCG and are allowed to mate. Six days after mating the uteri are removed therefrom. The uteri are immediately frozen and allowed to come to temperature equilibration with a low temperature environment and as solidified carbon dioxide (approximately $-78$ degrees C.) at atmoshpheric pressure. The uteri before or after freezing are cut into fine slivers with a scalpel. A Tris buffer solution of approximately 7.4 pH and one part per thousand by volume monothioglycerol is added to the tissue. The buffer is added preferably in approximately 5 parts by volume to on part of the tissue.

The tissue and buffer solution are placed in a laboratory blender of approximately five milliliter volume and agitated for ten seconds followed by a cooling period of approximately one minute in a low temperature bath after which agitation and cooling are repeated for approximately a total of three cycles. Thereafter, the mixture formed of the homogenized tissue and buffer solution is centrifuged in a low temperature environment for approximately one half hour at forty thousand revolutions per minute. A supernatant liquid is collected and separated into vials of desired sample size. The vials are submerged in liquid nitrogen and allowed to equilibrate therewith so as to freeze the supernatant. The frozen supernatant is placed in a vacuum produced by conventional freeze drying equipment and allowed to freeze dry into a dry flake. The vials are sealed before removal from the vacuum so as to subject the flakes to a substantially moisture and air free environment within the vial. Each vial contains a suitable sample for comparative testing during estrogen receptor assays.

EXAMPLE 2

The process according to example 1 is repeated except the tissue comprises corpora leutea collected during a luteal menstrual phase from a mammal. The resultant product of the process comprises a dry flake suitable for a control sample during comparative testing of progesterone receptors. It is noted that the homogenization process may be varied to produce the same result, that is for instance, the number of agitations could be increased and the duration of each agitation decreased. Likewise, the centrifugation process can be varied so that the revolutions per mintute is increased or decreased with a corresponding decrease or increase in the amount of time. Further, in like manner, the freezing temperatures may be varied within an appropriate range as may the pH of the buffer solution based upon the ability of the particular receptor protein to withstand such temperature and pH. variations.

EXAMPLE 3

It is further recognized that control samples of each of the steroid hormones not discussed in Examples 1 and 2 may be produced by the process according to Example 1 utilizing mammalian tissue known to contain the appropriate steroid receptors, as was discussed, for example, in the Summary of the Invention hereinabove.

It is understood that while certain embodiments of the present invention have been described herein, the invention is not to be limited to the specific embodiments so described.

What is claimed and desired to secure by Letters Patent is as follows:

1. An estrogen receptor control sample process for production of a control sample for use in estrogen receptor assays; said process comprising the steps of:
   (a) inducing superovulation in a female mammal in conjunction with mating of the mammal so as to produce pregnancy within the mammal;
   (b) thereafter collecting a mammalian tissue from said mammal containing estrogen receptors;
   (c) adding a buffer solution to said tissue;
   (d) homogenizing said tissue and said buffer together;
   (e) centrifuging said homogenized tissue and buffer; and
   (f) collecting the supernatant from said centrifuged tissue and buffer as said control sample.

2. The process according to claim 1 wherein said tissue is:
 (a) from the uterus of the mammal.
3. The process according to claim 1 wherein:
 (a) said superovulation is induced by the steps of:
 (b) injecting follicle stimulating hormone into the mammal on consecutive days; and thereafter
 (c) injecting human chorionic gonadotropin into said mammal.
4. The process according to claim 1 wherein:
 (a) said superovulation is induced by the steps of:
 (b) injecting pregnant mare's serum into the mammal on consecutive days; and
 (c) thereafter injecting luteinizing hormone into said mammal.
5. The process according to claim 1 including the steps of:
 (a) freezing said supernatant; and
 (b) subjecting said frozen supernatant to a vacuum so as to freeze dry said supernatant into dry flakes for use as said control sample.
6. The process according to claim 1 wherein:
 (a) the tissue is rabbit tissue collected from approximately 6 day pregnant rabbits.
7. The product produced by the process of claim 1.
8. A process for the production of a control sample for use in estrogen receptor assays; said process comprising the steps of:
 (a) inducing superovulation in rabbits;
 (b) in conjunction with such superovulation inducing pregnancy in the rabbits;
 (c) collecting uteri tissue from approximately 6 day pregnant rabbits following steps (a) and (b);
 (d) freezing said tissue;
 (e) shreading said tissue into relatively small strips;
 (f) adding a buffer solution having a pH of approximately 7.5 to said tissue;
 (g) homogenizing said buffer and tissue;
 (h) centrifuging said homogenized buffer and tissue;
 (i) removing the supernatant from said centrifuged buffer and tissue;
 (j) freezing said supernatant; and
 (k) subjecting said frozen supernatant to a vacuum so as to freeze dry said supernatant into dry flakes.
9. The product produced by the process of claim 8.
10. A process for the production of a control sample for use in estrogen receptor assays; said process comprising the steps of:
 (a) inducing superovulation in rabbits in conjunction with inducing pregnancy in such rabbits;
 (b) collecting uteri tissue from such rabbits after the rabbits have been pregnant for a period of approximately 6 days;
 (c) freezing said tissue to less than approximately −70 degrees C.;
 (d) shreading said tissue into relatively small strips;
 (e) adding a buffer solution having a pH of approximately 7.5 to said tissue;
 (f) homogenizing said buffer and tissue in a blender for periods of less than approximately ten seconds while allowing the tissue and buffer to be cooled between periods of homogenization until substantial homogenization occurs;
 (g) centrifuging said homogenized buffer and tissue;
 (h) removing the supernatant from said centrifuged buffer and tissue;
 (i) freezing said supernatant to less than about −70 degrees C.;
 (j) placing said supernatant in a plurality of approximately equal aliquots;
 (k) subjecting said frozen supernatant to a vacuum so as to freeze dry said supernatant into dry flakes; and
 (l) placing said dry flakes after freeze drying into a vacuum retaining container for storage until use as a control sample.

* * * * *